United States Patent [19]

Rosenkranz et al.

[11] 4,059,721

[45] Nov. 22, 1977

[54] STABILIZED ACRYLIC ACID ESTERS OF POLYHYDRIC ALCOHOLS AND A PROCESS FOR THEIR PREPARATION

[75] Inventors: Hans Jürgen Rosenkranz, Krefeld; Hans Rudolph, Krefeld-Bockum, both of Germany

[73] Assignee: Bayer Aktiengesellschaft, Germany

[21] Appl. No.: 597,168

[22] Filed: July 18, 1975

[30] Foreign Application Priority Data

July 24, 1974 Germany .............................. 2435509

[51] Int. Cl.$^2$ ............................................ C07C 69/54

[52] U.S. Cl. ...................................................... 560/205
[58] Field of Search ..................................... 260/486 R

[56] References Cited

U.S. PATENT DOCUMENTS 3,227,628   1/1966   Hess .................................. 260/486 R

*Primary Examiner*—Paul J. Killos
*Attorney, Agent, or Firm*—Connolly and Hutz

[57] ABSTRACT

Acrylic acid esters of polyhydric alcohols can be stabilized by the addition of allyl compounds.

7 Claims, No Drawings

STABILIZED ACRYLIC ACID ESTERS OF POLYHYDRIC ALCOHOLS AND A PROCESS FOR THEIR PREPARATION

The invention relates to stabilised, polymerisable acrylic acid esters containing at least two acrylic acid radicals and a process for their preparation from compounds containing several esterifiable hydroxyl groups, and acrylic acid.

Acrylic acid esters of polyhydric alcohols very easily tend to undergo undesired polymerisation. Polymerisation inhibitors which are in themselves known, such as phenols, phenol derivatives, copper, copper compounds and phenothiazine have already been used for stabilising these acrylic acid esters; however, the stabilisation achieved thereby has in many cases proved inadequate.

The inhibitors mentioned have also already been added to the reaction mixtures used for the preparation of the acrylic acid esters of polyhydric alcohols. Thus, it is known, from German Auslegeschrift (German Published Specification) 1,267,547 and from the journal "Chem. and Ind." 18 (1970), page 597, to prepare acrylic acid esters of polyhydric alcohols by azeotropic esterification of acrylic acid with polyhydric alcohols in the presence of the said polymerisation inhibitors and of said acid catalysts, concentrated sulphuric acid having been used as the acid catalyst and benzene as the entraining agent for the water of reaction. This process has the disadvantage that premature polymerisation during esterification can only be prevented by carrying out the process in the presence of relatively high amounts of inhibitors, which greatly lower the reactivity of the acrylic acid esters of polyhydric alcohols and accordingly make the preparation of polymerisation products from the monomeric compounds substantially more difficult.

It has now been found that small amounts of allyl compounds, especially in combination with polymerisation inhibitors which are in themselves known are outstandingly suitable for the stabilisation of acrylic acid esters of polyhydric alcohols against undesired polymerisations.

Accordingly, the subject of the invention is stabilised acrylic acid esters of polyhydric alcohols containing small amounts of allyl compounds, preferably in combination with known polymerisation inhibitors.

The content of allyl compounds in the acrylic acid esters of polyhydric alcohols in 0.001 to 5 percent by weight, preferably 0.01 to 1 percent by weight, and the content of the polymerisation inhibitors is preferably 0.01 to 0.3 percent by weight, calculated relative to the acrylic acid esters of polyhydric alcohols.

A further subject of the invention is a process for the preparation of stabilised acrylic acid esters of polyhydric alcohols by esterifying the acrylic acid with several compounds containing esterifiable hydroxyl groups, wherein the esterification is carried out in the presence of small amounts of allyl compounds, preferably in combination with known polymerisation inhibitors.

The esterification is preferably carried out under azeotropic conditions, and particularly suitable entraining agents for removing the water of reaction have proved to be aliphatic hydrocarbons or mixtures thereof, especially those boiling between 40° and 80° C, preferably between 50° and 70° C.

Furthermore it is advantageous to use, an esterification catalysts, acidic ion exchangers, preferably ion exchangers containing as acid groups, if appropriate in a macroporous form.

Suitable compounds with several esterifiable hydroxyl groups are practically all polyols customary in polyester chemistry. Examples which may be mentioned are dihydric and polyhydric, preferably di-, tri- and tetrahydric aliphatic and cycloaliphatic alcohols of which the aliphatic radicals can contain oxygen atoms as chain members, especially those with 2 to 20 carbon atoms. The following may be mentioned as examples: ethylene glycol, propylene glycol, butanediol, hexanediol, neopentyl glycol, diethylene glycol, triethylene glycol, dimethylolpropane, dimethylolcyclohexane, glycerol, trimethylolpropane, trimethylolhexane, trimethylolethane, 1,3,5-hexanetriol, pentaerythritol, dipentaerythritol and tripentaerythritol, mannitol and sorbitol. Polyethers, containing OH groups, or dihydric and polyhydric, preferably of di, tri- and tetrahydric alcohols, and polyesters of polyhydric alcohols and polybasic carboxylic acids are also suitable.

These compounds, and their mixtures, can be esterified stoichiometrically with acrylic acid, in accordance with the OH equivalent of the compounds, but it can be desirable, for example when using polyhydroxy compounds with more than two OH groups, such as trimethylolpropane or pentaerythritol, or when using sugar alcohols, only to esterify part of the OH groups present with acrylic acid. In that case, it is possible to use less acrylic acid than that which corresponds to the OH equivalent. However, in principle it is also possible to use excess acrylic acid in the esterification reaction. Even with an excess of only about 10 mol percent above the theoretically required amount, complete esterification of all OH groups present can be achieved. The excess acrylic acid can remain in the reaction mixture or can be removed, or converted, by various ways after the esterification, for example by a reaction with an epoxy compound.

As already explained, known polymerisation inhibitors, in combination with small amounts of allyl compounds, may be added to the acrylic acid esters of polyhydric alcohols or to the reaction mixture for the preparation of these esters, in order to avoid a premature polymerisation.

Suitable polymerisation inhibitors are, for example, those based on a phenol, such as hydroquinone, toluhydroquinone, benzoquinone, di-tert.-butyl-p-cresol, p-methoxyphenol or phenol, or phenothiazine, copper or copper compounds. Other suitable inhibitors are described in "Methoden der Organischen Chemie" (Methods of Organic Chemistry) (Houben-Weyl), 4th edition, Vol. XIV/1, pages 433–452, 456, Georg Thieme Verlag, Stuttgart 1961. These inhibitors are generally added to the reaction mixture before the beginning of the esterification process, in amounts of 0.01 to 0.3 percent by weight, calculated relative to the mixture of acrylic acid and polyhydroxy compound.

Allyl compounds have proved to be extremely effective stabilisers, without which it has hitherto not been possible, or only been possible with great effort, to obtain the acrylic acid ester of polyhydric alcohols without gel constituents and without turbidity, and at the same time with the high reactivity. Suitable allyl compounds are in particular those which because of their volatility are at least partially present in the gas space of the reaction vessel during the esterification process. Admittedly, nonvolatile allyl compounds, which because of their higher molecular weight are restricted to the liquid phase, also show a distinct stabilising action in the process of preparation according to the invention and above with regard to the storability of the finished product.

This finding is all the more surprising since it is known that allyl compounds, for example certain allyl esters, can themselves be polymerised by radical mechanisms. A stabilising effect of these compounds was in no way to be expected.

Suitable allyl compounds are compounds which contain one or more bonded radicals of the following formula I

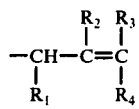

wherein
R$_{1-4}$ denote H or alkyl with 1 to 4 C,
R$_1$ preferably denotes H or methyl and
R$_{2-4}$ preferably denote H.

The radicals of the formula I can, for example, be bonded directly to a halogen atom, especially chlorine or bromine, to a hydroxyl group or to radicals of monohydric or polyhydric alcohols or phenols or to radicals of monobasic or polybasic, optionally olefinically unsaturated, carboxylic acids, with substitution of the hydrogen atoms of these radicals and formation of ether or ester groupings via the hydroxyl or carboxyl groups of the radicals, respectively; optionally, in the case of polyhydric alcohols or polycarboxylic acids, a part of the hydroxyl groups or of the carboxyl groups is unsubstituted.

Examples of suitable allyl compounds can be represented by the following formula:

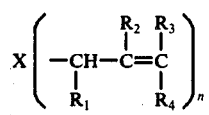

wherein
R$_1$ to R$_4$ have the above meaning,
X denotes chlorine, bromine, —OH, —O— or a radical of the formula

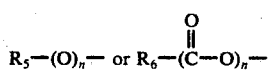

wherein
R$_5$ denotes a n-valent, optionally free hydroxyl-containing or ether-containing aliphatic, araliphatic, cycloaliphatic or aromatic radical, preferably with not more than 12 C atoms, and
R$_6$ denotes a n-valent, optionally olefinically unsaturated aliphatic radical or a n-valent cycloaliphatic, araliphatic or aromatic radical and n denotes the number 1 when X = Cl, Br or —OH, and denotes an integer from 1 to 4, preferably 1 to 3, in the other cases.

The molecular weight of the allyl compounds is between 58 and 600, preferably between 58 and 300.

Special examples of suitable allyl compounds are: allyl chloride, allyl bromide, diallyl ether, allyl ethers of monohydric aliphatic, cycloaliphatic or araliphatic alcohols and monohydric phenols with, preferably, not more than 12 carbon atoms, such as allyl ethyl ether, allyl butyl ether, allyl dodecyl ether, allyl cyclohexyl ether, allyl benzyl ether and allyl phenyl ether; allyl ethers of polyhydric aliphatic, cycloaliphatic and araliphatic alcohols or phenols with not more than 4, preferably not more than 3, etherified hydroxyl groups, it being possible for these esters to contain free hydroxyl groups and the alcohols or phenols to contain ether groupings, such as the monoallyl and diallyl ethers of ethylene glycol, diethylene glycol, triethylene glycol, propylene glycol, butylene glycol and hexylene glycol and the monoallyl, diallyl and triallyl ethers of trimethylolpropane; allyl esters of monobasic and polybasic, optionally olefinically unsaturated, aliphatic carboxylic acids and of monobasic and polybasic cycloaliphatic, araliphatic and aromatic carboxylic acids of which the aliphatic, cycloaliphatic, araliphatic or aromatic radicals preferably contain not more than 12 C atoms, such as allyl acetate, allyl propionate, allyl acrylate and allyl benzoylate; diallyl esters of the benzenedicarboxylic acids; and also the derivatives of methallyl alcohol and crotyl alcohol corresponding to the said allyl halides, allyl ethers and allyl esters, such as crotyl alcohol, crotyl ethyl ether, crotyl phenyl ether, crotyl acetate, methallyl alcohol, methallyl ethyl ether, methallyl phenyl ether and methallyl acetate. Allyl alcohol is particularly preferred.

The compounds can be added to the esterification mixture of acrylic acid and polyhydric alcohols in amounts of 0.001 to 5 percent by weight, preferably 0.01 to 1 percent by weight. It is particularly advantageous to introduce the allyl compounds continuously during the esterification process, either by constant dropwise addition or by blowing in allyl compounds by means of gases, for example nitrogen or air. Allyl alcohol, which can be introduced into the reaction in sufficient amount by means of a stream of air, is particularly suitable for the latter method.

The esterification process according to the invention is carried out in the presence of an aliphatic hydrocarbon or hydrocarbon mixture of preferred boiling range of 50° to 70° C. It should be emphasised particularly that the actual reaction mixture, consisting of polyol and acrylic acid, is not miscible with this solvent, at least at a low temperature.

Examples of suitable aliphatic hydrocarbons in this context are hexane and its isomers, and cyclohexane, but preferably all hydrocarbon mixtures which can also contain higher-boiling or low-boiling hydrocarbons, such as pentane or heptane, and which boil in the desired temperature range. The amount of added hydrocarbon or hydrocarbon mixture is in no way critical; depending on the apparatuses used, in which the esterification is carried out, the amount added can be chosen to be between 0.05 times and twice the amount of the reaction mixture. A ratio, of the amount of esterification mixture to the amount of hydrocarbon or hydrocarbon mixture, of 1:0.1 to 1:05, is advantageous.

The hydrocarbon solvent serves as an entraining agent in the esterification process, for the purpose of removing the liberated water from the system. Accordingly, the esterification according to the invention must be carried out under apparatus conditions which permit separation and removal from the system of the water of reaction. Usually, the customary water separators are used for this purpose.

Catalysts used for the process of preparation of the new polyfunctional acrylic acid esters, according to the invention, are commercially available acid ion exchange resins, preferably those containing sulphonic acid groups as ion exchange groups. The catalysts can be employed in from 0.005 times the amount of reaction mixture to amounts equal to the amount of reaction mixture, preferably in 0.05 to 0.2 times the amount of the reaction mixture.

A typical method of preparation of the polyfunctional acrylic acid esters stabilised in accordance with the invention consists, for example, of heating under reflux the desired mixture of acrylic acid, polyhydroxy compound and polymerisation inhibitor, in a stirred vessel equipped with heating and with a device for the azeotropic separation of water, together with the acid ion exchanger and the amount of hydrocarbon mixture required to remove the water from the system, whilst constantly introducing a quantity of allyl compound. The amount of water separated off, and the decrease in the content of free acrylic acid, which can easily be determined by titration, provides information on the progress of the esterification reaction. When the content of free acrylic acid has reached the desired level, the reaction is discontinued and the hydrocarbon mixture which serves as the entraining agent for the water of reaction is distilled off. Remnants of hydrocarbon mixture can be removed under reduced pressure. The acid ion exchanger is removed by filtration and the polyfunctional acrylic acid ester according to the invention is then ready for use as a lacquer raw material for curing by electron beams, in printing inks which are cured by UV light, in plastic printing plates or in moulding or casting compositions. However, the use of these products is in no way restricted to the applications mentioned here; the products can in principle be used wherever polyfunctional acrylic acid esters or methacrylic acid esters have also hitherto been employed as crosslinking agents.

In carrying out the esterification process according to the invention, a washing process to remove the esterification catalyst is superfluous; the stabilisation with conventional types of stabilisers which reduce the reactivity, for example phenolic compounds or copper compounds, can be reduced to a level which has no adverse influence on the reactivity of the product. Furthermore, the present process permits the preparation of the polyfunctional acrylic acid esters on an industrial scale. Even when batches of the order of magnitude of several tons are manufactured, the esterification can be carried out without any problems in the manner herein before described.

A further advantage of the process according to the invention results, surprisingly, from the fact that the reactants, namely acrylic acid and polyhydroxy compound, are immiscible with the hydrocarbon or hydrocarbon mixture. A comparison with an esterification in benzene shows that the rate of esterification is increased substantially. This fact also assists industrial utilisation of the process according to the invention.

A continuous process is equally feasible if the criteria according to the invention are taken into account. By constantly feeding in acrylic acid, polyhydroxy compound, stabilisers and hydrocarbon mixture and at the same time removing the finished esterified product, it is possible to set up a stationary state which, because of the very good heat stability of the polyfunctional acrylic acid esters according to the invention, can be maintained practically indefinitely without a polymerisation occurring.

The illustrative embodiments which follow are intended to explain the invention in more detail.

EXAMPLE 1

1,4-Butanediol bis-acrylate:

6.76 kg of 1,4-butanediol, 10.8 kg of acrylic acid, 1.3 kg of an acid ion exchanger (Lewatit 3333 of BAYER AG), 22.8 of p-methoxyphenol and 3 liters of a petroleum ether fraction boiling in the range from 60° to 70° C were heated to the boil under a water separator, in a 25 liter stirred kettle equipped with a water separator, whilst stirring, passing in air and at the same time adding dropwise 100 g of allyl alcohol, over the entire duration of the esterification. After a time of 62 hours, in which the boiling point of the mixture had risen from an initial value of 63° C to a final value of 70° C, an acid number of 25 was found by titration of a sample, and the reaction was discontinued. At that stage, 2.36 liters of $H_2O$ had been separated off. The petroleum ether was distilled off initially under normal pressure and then under reduced pressure. The product was freed from the esterification catalyst by filtration and the catalyst was used for further esterifications. 1.45 kg of a clear, practically colourless 1,4-butanediol bis-acrylate were obtained, having a high reactivity when cured under the influence of electron beams. The viscosity corresponding to a time of outflow of 11 seconds, measured in a DIN cup 4, at 20° C.

EXAMPLE 2

Trimethylolpropane triacrylate:

2.44 kg of trimethylolpropane, 3.93 kg of acrylic acid, 0.5 kg of an acid ion exchanger (Lewatit 3333 of BAYER AG), 9 g of hydroquinone and 1.5 liters of petroleum ether (boiling range 60° to 70° C) were heated under a water separator, whilst stirring, in a 10 liter three-necked flask equipped with a stirrer, water separator and gas inlet tube. At the same time, a constant stream of air saturated with allyl alcohol was passed through the flask at a rate of 2 liters/hour. In total, 16 ml of allyl alcohol were introduced into the esterification mixture in this way. After 80 hours, the reaction mixture had an acid number of 32 and the boiling point had risen to 72° C. The petroleum ether was distilled off, remnants being removed by applying a vacuum of 0.2 mm Hg at a product temperature of 40° C. The esterification catalyst was separated off by filtration and was kept for further use. The trimethylolpropane triacrylate obtained in practically quantitative yield was pale yellowish and clear. The viscosity corresponded to a time of outflow of 20 seconds measured in a DIN cup 4 at 20° C. The product showed no change even on storage for 4 months at 60° C. When used in a UV light-curing printing ink which contained a photoinitiator, the product polymerised at high speed.

EXAMPLE 3

Trimethylolpropane triacrylate was prepared analogously to Example 2, 46 g of allyl chloride being introduced, instead of the allyl alcohol with the air passed in. This product again showed the desired good stability on storage.

EXAMPLE 4

Trimethylolpropane triacrylate was prepared analogously to Example 2, 60 g of trimethylolpropane diallyl ether being added to the mixture at the beginning of the esterification, but only air being passed through subsequently. This product again was practically colourless and clear and showed good reactivity in an electron beam-induced polymerisation.

EXAMPLE 5 (comparison example)

If the esterification according to Example 2 was carried out without addition of allyl compounds, gel-like crusts formed on the stirrer and on the wall of the vessel during the reaction. The product was cloudy and gelled after 2 days at 60° C.

EXAMPLE 6

Butanediol/trimethylolpropane mixed acrylate: 4.03 kg of trimethylol propane, 2.7 kg of 1,4-butanediol and 10.8 kg of acrylic acid were esterified under a water separator, as described in Example 1, in the presence of 22 g of phenothiazine, 1.3 kg of an acid ion exchanger and 3 liters of a light benzine fraction boiling at 60° to 70° C. Here again the mixture was stabilised additionally by constant dropwise addition of a total of 100 ml of allyl alcohol. 14.5 kg of a stable mixed acrylate of acid number 25 were obtained.

EXAMPLE 7

A mixed ester of acrylic acid with trimethylolpropane and 1,3-propanediol can also be obtained analogously to Example 6. In this case, the reaction time is extended to about 90 hours.

EXAMPLE 8

136.2 g of pentaerythritol, 288.3 g of acrylic acid, 30 g of an acid ion exchanger (Lewatit 3333 of BAYER AG), 0.5 g of p-methoxyphenol and 110 ml of petroleum ether (fraction boiling at 60° to 70° C) were heated to the reflux temperature in a 1 liter three-necked flask equipped with a gas inlet tube, stirrer and water separator. During the esterification, which had progressed over the course of 48 hours to the point that the acid number of the mixture was 35, a total of 5 g of crotyl alcohol was added dropwise. After evaporating off the petroleum ether and filtering off the acid ion exchange resin, a pale yellow, clear pentaerythritol tetraacrylate was obtained. The content of residual free acrylic acid was lowered to a value corresponding to acid number 5 by washing with distilled water.

EXAMPLE 9

A diacrylate of neopentyl glycol and acrylic acid was prepared analogously to Example 1. The stabilisation was achieved with corresponding amounts of benzoquinone and acetic acid allyl ester.

EXAMPLE 10

Trimethylolpropane diacrylate: 2.68 kg of trimethylolpropane, 3.03 kg of acrylic acid, 0.5 kg of an acid ion exchanger (Lewatit 3333 of BAYER AG), 9 g of hydroquinone monomethyl ether and 1.5 liters of petroleum ether (boiling range 60° to 70° C) were heated under a water separator, whilst stirring, in a 10 liter three-necked flask equipped with a stirrer, water separator and gas inlet tube. At the same time, a constant stream of air was passed through the flask at about 2 liters/hour. Over the course of the entire reaction time of 72 hours, during which an acid number of 17 was reached, a total of 20 ml of diallyl phthalate was added dropwise to the reaction mixture. The petroleum ether was distilled off, remnants being removed by applying a vacuum of approx. 4 mm Hg at a product temperature of 40° C. The esterification catalyst was filtered off. The resulting trimethylolpropane diacrylate mixture was pale yellowish and clear. The viscosity corresponded to a time of outflow of 186 seconds, measured in a DIN cup 4, at 20° C.

EXAMPLE 11

Pentaerythritol diacrylate:
Pentaerythritol diacrylate was prepared analogously to Example 10, a total of 20 g of phenyl allyl ether being introduced continuously during the entire esterification time. The product was sightly yellowish in colour, and clear. The viscosity corresponded to a time of outflow of 246 seconds, measured in the DIN cup 4, at 20° C. This product also showed no change after 3 week's storage at 60° C.

EXAMPLE 12

Trimethylolpropane triacrylate was prepared analogously to Example 2, 30 g of diallyl ether being introduced, instead of the allyl alcohol, by means of the air passed in. This product was again clear and very reactive when cured with UV light, and had good stability on storage.

We claim:
1. A composition comprising an acrylic acid ester of a polyhydric alcohol having at least two acrylate moieties and a stabilizing amount of an allyl compound of the formula

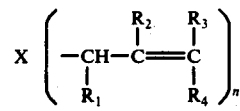

wherein $R_1$–$R_4$ are hydrogen or alkyl having 1 to 4 carbon atoms;
X is chlorine, bromine, hydroxy,

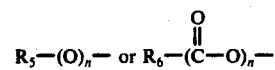

wherein $R_5$ is an n-valent aliphatic, araliphatic, cycloaliphatic or aromatic hydrocarbon radical which may contain free hydroxy moieties or —O— linking moieties and $R_6$ is an n-valent aliphatic, cycloaliphatic, araliphatic or aromatic radical and n is an integer of from 1 to 4.

2. The composition of claim 1 wherein $R_1$ is hydrogen or methyl and $R_2$-$R_4$ is hydrogen.

3. The composition of claim 1 including a polymerization inhibitor.

4. The composition of claim 1 wherein X is hydroxyl.

5. A process for preparing a stabilized acrylic acid ester of a polyhydric alcohol which comprises esterifying at least two hydroxyl moieties of a polyhydric alcohol with acrylic acid in the presence of a stabilizing amount of an allyl compound of the formula

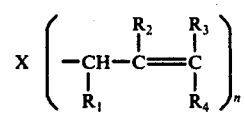

wherein $R_1$-$R_4$ are hydrogen or alkyl having 1 to 4 carbon atoms; X is chlorine, bromine, hydroxy,

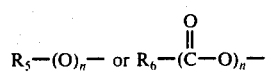

wherein $R_5$ is an n-valent aliphatic, araliphatic, cycloaliphatic or aromatic hydrocarbon radical which may contain free hydroxy moieties or —O— linking moieties and $R_6$ is an n-valvent aliphatic, cycloaliphatic, araliphatic or aromatic radical and $n$ is an integer of from 1 to 4.

6. The process of claim 5 wherein said esterification is carried out under azeotropic conditions in the presence of at least one aliphatic hydrocarbon having a boiling point between about 40° and 80° C. as the entraining agent for removing water of reaction.

7. The process of claim 5 wherein an acid ion exchange resin is used as esterification catalyst.

* * * * *